(12) United States Patent
Sakai et al.

(10) Patent No.: US 7,258,772 B2
(45) Date of Patent: Aug. 21, 2007

(54) OXYGEN SENSOR AND METHOD OF MANUFACTURING SAME

(75) Inventors: Shoichi Sakai, Atsugi (JP); Futoshi Ichiyanagi, Atsugi (JP)

(73) Assignee: Hitachi, Ltd., Tokyo-to (JP)

( * ) Notice: Subject to any disclaimer, the term of this patent is extended or adjusted under 35 U.S.C. 154(b) by 635 days.

(21) Appl. No.: 10/431,534

(22) Filed: May 8, 2003

(65) Prior Publication Data

US 2003/0213692 A1  Nov. 20, 2003

(30) Foreign Application Priority Data

May 17, 2002  (JP)  ............................. 2002-142749
May 17, 2002  (JP)  ............................. 2002-143154

(51) Int. Cl.
*G01N 27/409*  (2006.01)
*G01N 27/41*  (2006.01)

(52) U.S. Cl. ...................... 204/425; 204/429; 73/23.32

(58) Field of Classification Search ............... 204/424, 204/425, 429; 205/784; 73/23.32
See application file for complete search history.

(56) References Cited

U.S. PATENT DOCUMENTS

| 4,264,425 A | * | 4/1981 | Kimura et al. ............... 204/412 |
| 4,304,652 A | * | 12/1981 | Chiba et al. ................. 204/425 |
| 4,306,957 A | * | 12/1981 | Ishitani et al. .............. 204/412 |
| 4,391,691 A |   | 7/1983 | Linder et al. |
| 4,496,455 A |   | 1/1985 | Linder et al. |
| 4,510,036 A | * | 4/1985 | Takeuchi et al. ............ 204/425 |
| 4,718,999 A |   | 1/1988 | Suzuki et al. |
| 4,765,880 A | * | 8/1988 | Hayakawa et al. ......... 204/425 |
| 5,447,618 A | * | 9/1995 | Sugiyama et al. .......... 204/426 |
| 5,507,174 A |   | 4/1996 | Friese et al. |
| 6,096,187 A |   | 8/2000 | Mizoguchi et al. |
| 6,214,209 B1 |  | 4/2001 | Gruenwald |
| 6,355,151 B1 |  | 3/2002 | Brosda et al. |

FOREIGN PATENT DOCUMENTS

| DE | 44 39 901 C2 | 11/1994 |
| DE | 198 24 316 A1 | 6/1998 |
| JP | 61-047553 A | 3/1986 |
| JP | 61-100651 A | 5/1986 |

* cited by examiner

*Primary Examiner*—Kaj K. Olsen
(74) *Attorney, Agent, or Firm*—Sughrue Mion, PLLC

(57) ABSTRACT

In an oxygen sensor that measures a limiting current of when a voltage is applied between pumping electrodes, and also performs a rich/lean judgment based on an electromotive force generated between one of the pumping electrodes and a reference electrode, an oxygen supply voltage for supplying oxygen to the reference electrode is applied, and the reference electrode is covered with a dense layer.

11 Claims, 7 Drawing Sheets

OXYGEN SENSOR AND METHOD OF MANUFACTURING SAME

FIELD OF THE INVENTION

The present invention relates to an oxygen sensor to be used for detecting an air-fuel ratio of combustible mixture based on an oxygen concentration in an exhaust gas of an internal combustion engine, and a method of manufacturing the same.

RELATED ART OF THE INVENTION

Heretofore, there has been known an oxygen sensor detecting an air-fuel ratio based on an oxygen concentration in an exhaust gas of an internal combustion engine.

An oxygen sensor disclosed in Japanese Unexamined Patent Publication No. 61-100651 is configured so that pumping electrodes are provided with an oxygen ion conductive electrolyte layer therebetween, and a reference electrode is provided facing one of the pumping electrodes with the oxygen ion conductive electrolyte layer therebetween.

Then, in this oxygen sensor, a limiting current of when a voltage is applied between the pumping electrodes is measured, and also, it is judged based on a voltage of the reference electrode whether an air-fuel ratio is rich or lean.

However, in such a conventional oxygen sensor, there is a problem in that, due to a variation of voltage property in the reference electrode or the flowing of a pumping current into the reference electrode, accuracy of rich/lean judgment is degraded.

SUMMARY OF THE INVENTION

Therefore, an object of the present invention is to enable to perform stably and accurately a rich/lean judgment of an air-fuel ratio based on a voltage of a reference electrode.

In order to achieve the above object, according to the present invention, there is provided an oxygen supply power source that applies a voltage for supplying oxygen to a reference electrode, between the reference electrode and a pumping electrode facing the reference electrode with a solid electrolyte layer therebetween, and there is also provided a dense layer covering the reference electrode.

Further, according to the present invention, a dense layer dividing a solid electrolyte layer disposed between a reference electrode and a pumping electrode that is disposed in parallel with the reference electrode.

The other objects and features of this invention will become understood from the following description with reference to the accompanying drawings.

PREFERRED EMBODIMENTS

Figure 1:
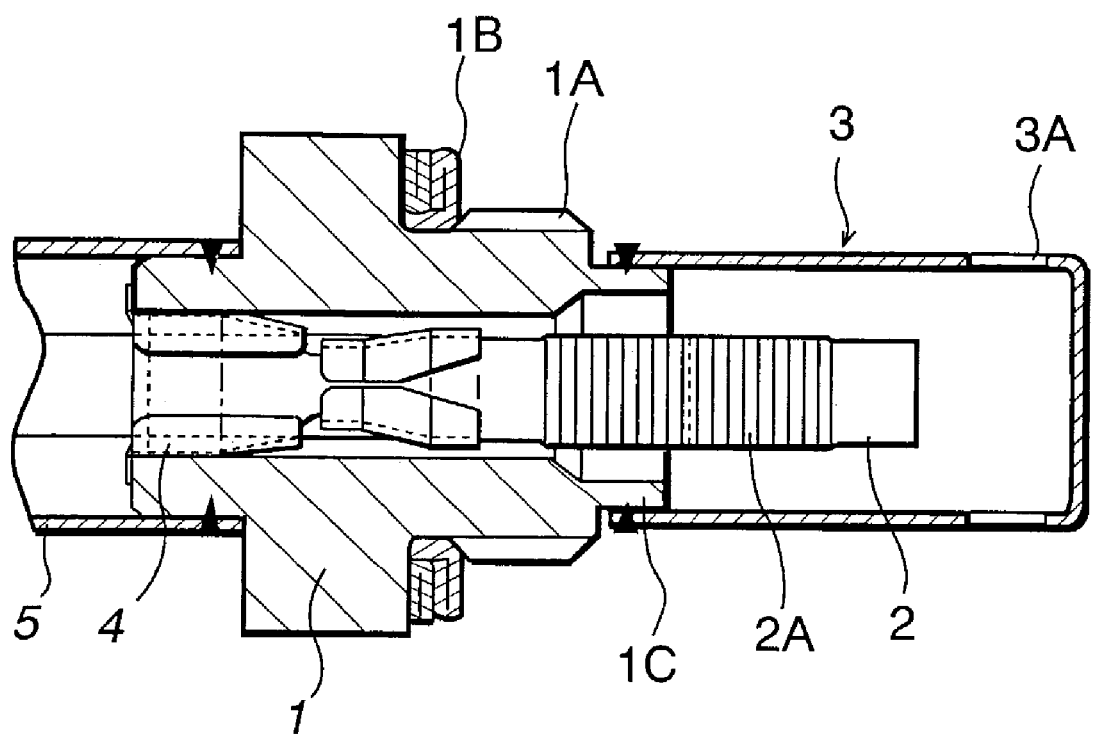
FIG. 1 is a cross sectional view of an oxygen sensor.

FIG. 1 is a cross sectional view of an oxygen sensor in an embodiment.

The oxygen sensor is mounted to an exhaust pipe of an internal combustion engine, for detecting an air-fuel ratio of the engine.

The oxygen sensor shown in FIG. 1 consists of a holder 1, a sensor element 2, a protector 3, a contact flange 4, a case 5 and the like.

Holder 1 is formed from metal, such as stainless steel, in a stepped cylinder shape, and is formed with, on a periphery at a tip end side thereof, a male screw portion 1A serving as a mounting portion.

Then, male screw portion 1A is tightened into a female screw portion serving as a mounting hole disposed in the exhaust pipe of the internal combustion engine so that the oxygen sensor is attached to the exhaust pipe.

Sensor element 2 is formed in a rod shape and is provided with, at a tip end side thereof, a sensing portion 2A to be described below.

Protector 3 is formed from a high heat resisting metal plate or the like, and holes 3A for introducing an engine exhaust gas are formed on protector 3 at plural points.

Protector 3 is fixed by welding to a tip end portion 1C of holder 1.

Sensing portion 2A of sensor element 2 is arranged within protector 3.

Sensing portion 2A is exposed to the exhaust gas (gas to be measured) introduced via protector 3, so that the air-fuel ratio of the engine (an oxygen concentration in the gas to be measured) is detected.

Rod shaped sensor element 2 is assembled to holder 1 via cylindrical contact flange 4.

Assembling of sensor element 2 to holder 1 is performed such that sensor element 2 is forced into contact flange 4, and further, contact flange 4 into which sensor element 2 is forced, is forced into holder 1.

Case 5 is formed from a high heat resisting metal plate or the like, and is fixed by welding to a base end portion of holder 1.

Leads to be connected to a heater pattern constituting sensing portion 2A and to electrodes are lead out from a base end side of case 5.

Figure 2:
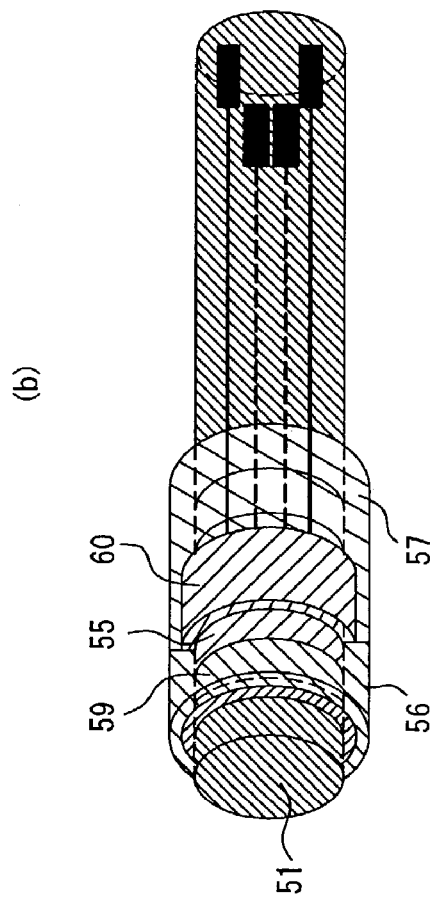
FIG. 2 shows a first embodiment of a sensor element, in which (A) is a cross sectional view and (B) is a perspective view.
Figure 2:
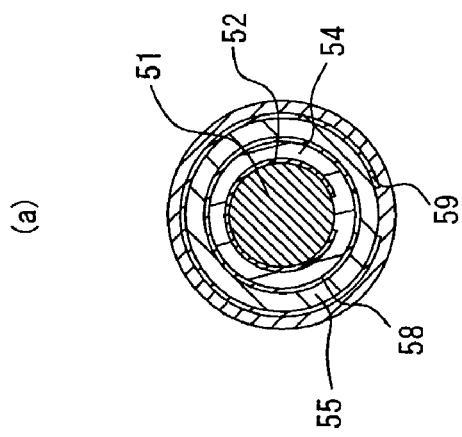
Figure 3:
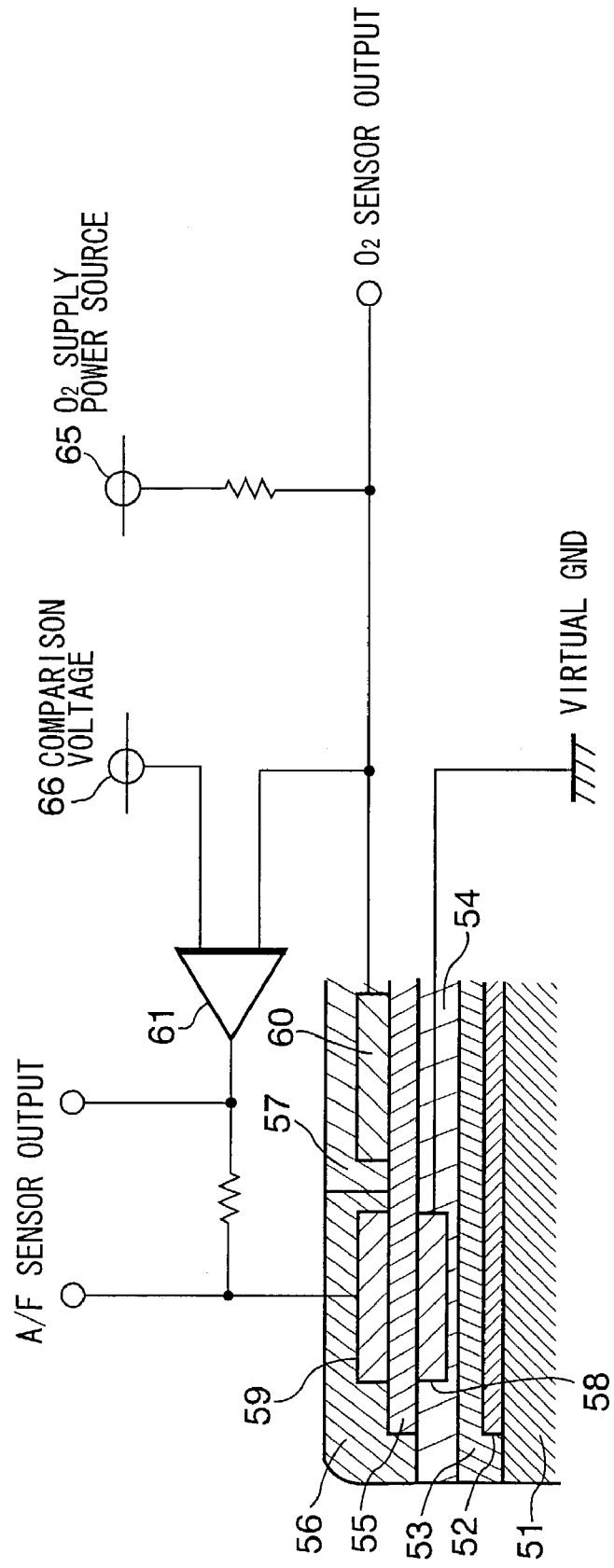
FIG. 3 is an enlarged cross sectional view of a sensing section of the sensor element shown in FIG. 2.

FIGS. 2 and 3 are diagrams showing a first embodiment of sensing portion 2A.

Sensing portion 2A is constituted by laminating annularly, a heater pattern 52, an alumina insulating layer 53, a first gas diffusion layer 54 and a dense zirconia solid electrolyte layer 55 having an oxygen ion conductivity, in this sequence, on a periphery of an alumina rod 51.

A second pumping electrode 59 formed from platinum or the like is disposed annularly on the outside of zirconia solid electrolyte layer 55.

A first pumping electrode 58 formed from platinum or the like is disposed annularly on the inside of zirconia solid electrolyte layer 55 facing second pumping electrode 59.

Further, a reference electrode 60 formed from platinum or the like is disposed annularly on the outside of zirconia solid electrolyte layer 55.

A second gas diffusion layer 56 and a dense layer 57 are disposed in parallel with each other in an axial direction, and cover a periphery of zirconia solid electrolyte layer 55, such that the portion disposed with second pumping electrode 59 is covered with second diffusion layer 56, and the portion disposed with reference electrode 60 is covered with dense layer 57.

Note, dense layer 57 is formed from mullite series (silica added) alumina with an average grain size of 0.3 to 0.5 µm.

First and second gas diffusion layers 54 and 56 are formed from alumina and zirconia based ceramic mixed powder with an average grain size of 0.4 to 0.8 µm.

First pumping electrode 58 is connected to a virtual ground (for example, the reference potential of about 1.5V).

Reference electrode 60 is connected with an oxygen supply power source 65 for applying a voltage that transports oxygen toward reference electrode 60.

Here, a voltage of reference electrode 60 is varied depending on a difference between an oxygen partial pressure of first pumping electrode 58 and an oxygen partial pressure of reference electrode 60.

That is, in the case where the air-fuel ratio is leaner than a stoichiometric air-fuel ratio, and a large amount of oxygen is present in the exhaust gas, oxygen is diffused to first pumping electrode 58 via first gas diffusion layer 54.

Therefore, although oxygen is transported toward reference electrode 60 from first pumping electrode 58 as a result of voltage application by oxygen supply power source 65, the difference between the oxygen partial pressure of first pumping electrode 58 and the oxygen partial pressure of reference electrode 60 becomes small.

Accordingly, in the case where the air-fuel ratio is leaner than the stoichiometric air-fuel ratio, an electromotive force generated between first pumping electrode 58 and reference electrode 60 due to the difference between the oxygen partial pressures, becomes small.

On the other hand, in a state where the air-fuel ratio is richer than the stoichiometric air-fuel ratio and the oxygen amount in the exhaust gas is little, the oxygen partial pressure of first pumping electrode 58 is lowered.

However, oxygen transported toward reference electrode 60 from first pumping electrode 58, is filled in dense layer 57 that covers reference electrode 60, so that the oxygen partial pressure of reference electrode 60 is stably maintained at a high level.

Therefore, the difference between the oxygen partial pressure of first pumping electrode 58 and the oxygen partial pressure of reference electrode 60 becomes large, and due to this large difference between the oxygen partial pressures, a large electromotive force is generated between first pumping electrode 58 and reference electrode 60.

As described in the above, since reference electrode 60 is connected with oxygen supply power source 65 in order to transport oxygen, and is covered with dense layer 57, it is possible to maintain the oxygen partial pressure of reference electrode 60 stably at a high level without a material influence of a change in air-fuel ratio.

Figure 4:
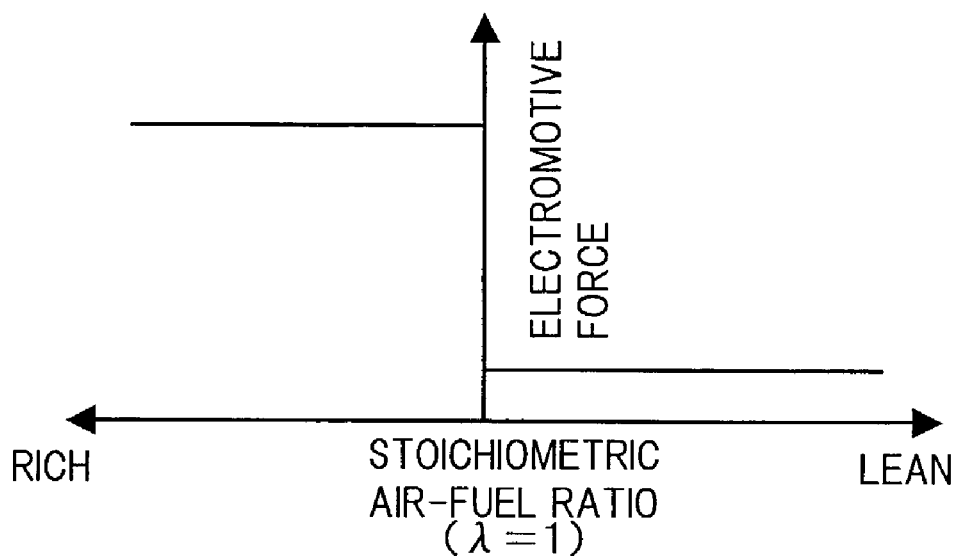
FIG. 4 is a graph showing a correlation between an electromotive force and an air-fuel ratio in the sensor element shown in FIG. 2.

Thus, the voltage of reference electrode 60 can be made to have a stable output characteristic that is switched in on/off manner depending on the rich/lean of air-fuel ratio (refer to FIG. 4).

The voltage of reference electrode 60 is output as a stoichiometric air-fuel ratio sensor output (rich/lean output), and also output to a comparator 61.

Then, in comparator 61, the voltage of reference electrode 60 is compared with a predetermined comparison voltage 66 (stoichiometric air-fuel ratio equivalent voltage).

When the air-fuel ratio is rich, and the voltage of reference electrode 60 is higher than comparison voltage 66, comparator 61 outputs a voltage (for example, 1V) lower than a voltage of first pumping electrode 58, as a pumping voltage.

On the other hand, when the air-fuel ratio is lean, and the voltage of reference electrode 60 is lower than comparison voltage 66, comparator 61 outputs a voltage (for example, 2V) higher than the voltage of first pumping electrode 58, as the pumping voltage.

Here, the potential of first pumping electrode 58 is fixed to the virtual ground (for example, the reference potential of about 1.5V).

Therefore, the pumping voltage is switched between a voltage higher than the virtual ground and a voltage lower than the virtual ground depending on the rich/lean of air-fuel ratio, so that directions of potential between pumping electrodes 58 and 59 can be switched.

As described in the above, it is possible to make the voltage of reference electrode 60 to be the stable output that is switched in on/off manner depending on the rich/lean of air-fuel ratio, and therefore, the switching of pumping voltage based on a rich/lean judgment of air-fuel ratio can be performed with high accuracy.

An output voltage of comparator 61 is applied to second pumping electrode 59.

For example, in the rich air-fuel ratio state where oxygen in the exhaust gas is little, and concentrations of hydrogen ($H_2$), carbon monoxide (CO) and hydrocarbon (HC) are high, electrons are given to carbon dioxide and water in second pumping electrode 59 being on a cathode side, to generate oxygen ions.

The oxygen ions are transported via solid electrolyte layer 55 toward first pumping electrode 58 being on an anode side.

Then, in first pumping electrode 58, the transported oxygen ions, and carbon monoxide and hydrogen in the exhaust gas react with each other, to be decomposed into carbon dioxide, water and electrons.

That is, by transporting the oxygen toward first pumping electrode 58, the difference between the oxygen partial pressure of reference electrode 60 and the oxygen partial pressure of first pumping electrode 58 is controlled to be smaller.

In other words, a control is performed so that the rich/lean judgment of air-fuel ratio based on the voltage of reference electrode 60 is reversed from the rich judgment to the lean judgment.

On the other hand, in the lean air-fuel ratio state where a large amount of oxygen remains in the exhaust gas, in first pumping electrode 58 being on the cathode side, electrons are given to the oxygen remaining in the exhaust gas, to generate oxygen ions.

Then, the oxygen ions are transported via solid electrolyte layer 55 toward second pumping electrode 59 being on the anode side, to be decomposed into oxygen and electrons in second pumping electrode 59.

That is, by transporting the oxygen toward second pumping electrode 59, the difference between the oxygen partial pressure of reference electrode 60 and the oxygen partial pressure of first pumping electrode 58 is controlled to be larger.

In other words, a control is performed so that the rich/lean judgment of air-fuel ratio based on the voltage of reference electrode 60 is reverted from the lean judgment to the rich judgment.

A limiting current (pumping current) Ip flowing between pumping electrodes 58 and 59, voltage directions of which are switched depending on the rich/lean of air-fuel ratio in the above manner, is linearly changed relative to the change in air-fuel ratio with the stoichiometric air-fuel ratio as a reference.

Accordingly, the limiting current (pumping current) Ip is detected as a terminal voltage of a current detection resistor R, to be output as an air-fuel ratio sensor output, so that the air-fuel ratio can be obtained based on the stoichiometric air-fuel ratio sensor output and the air-fuel ratio sensor output.

In the above embodiment, the sensor element of rod shape has been used, however, a similar effect can be achieved with a similar constitution if a sensor element of plate shape is used.

Note, by forming the sensor element in the rod shape, the oxygen concentration can be detected with stable accuracy without being influenced by the mounting direction of the sensor or the flowing direction of the gas to be detected.

Further, since the sensor element of the rod shape has the thermal shock resistance, a rate of cracks due to overwash can be remarkably reduced.

Figure 5:
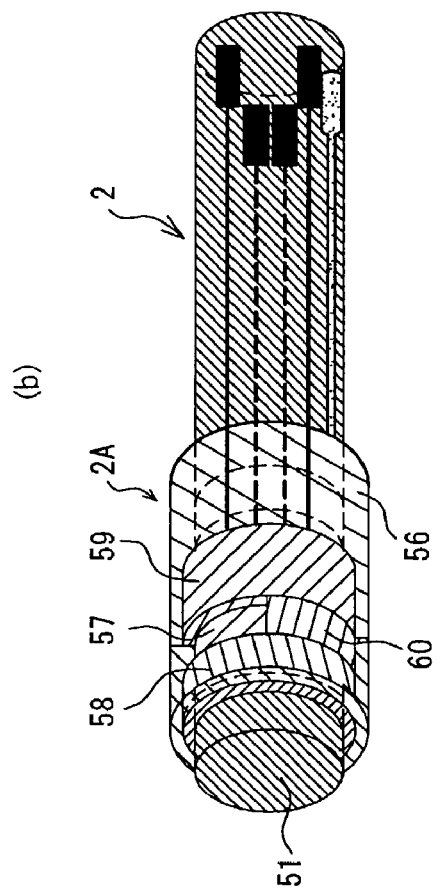
FIG. 5 is a second embodiment of the sensor element, in which (A) is a cross sectional view and (B) is a perspective view.
Figure 5:
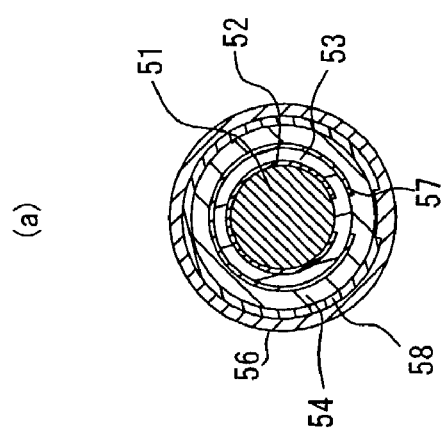
Figure 6:
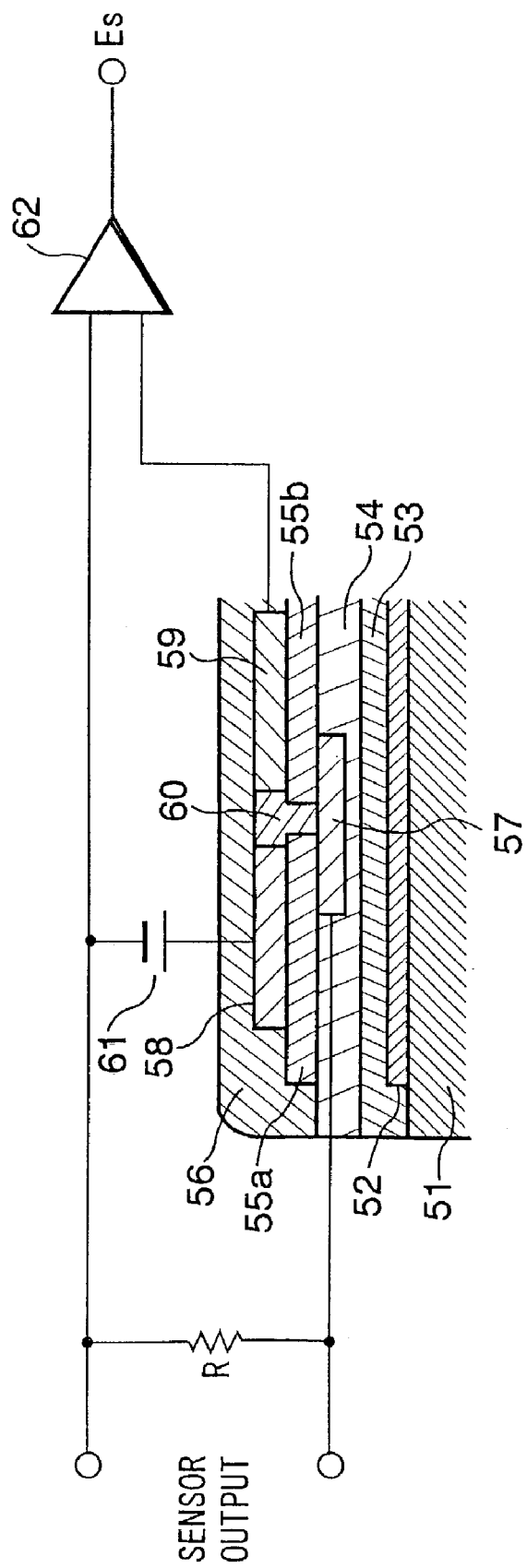
FIG. 6 is an enlarged cross sectional view of a sensing section of the sensor element shown in FIG. 5.

FIGS. 5 and 6 are diagrams showing a second embodiment of sensing portion 2A.

Sensing portion 2A is constituted by laminating a heater pattern 52, an alumina insulating layer 53, a first gas diffusion layer 54, a zirconia solid electrolyte layer 55 having an oxygen ion conductivity and a second gas diffusion layer 56, in this sequence, on a periphery of an alumina rod 51 as a base.

Zirconia solid electrolyte layer 55 is divided into two layers 55a and 55b along an axial direction.

Further, on the inside of zirconia solid electrolyte layer 55, a cathode electrode 57 (pumping electrode) formed from platinum or the like is disposed annularly so as to be across two layers 55a and 55b.

Spacing between two layers 55a and 55b is about 0.3 to 0.5 mm.

Moreover, an anode electrode 58 (pumping electrode) formed from platinum or the like is disposed annularly on a position to face cathode electrode 57 with layer 55a therebetween.

Moreover, a reference electrode 59 formed from platinum or the like is disposed annularly on a position to face cathode electrode 57 with layer 55b therebetween.

Furthermore, a dense layer 60 formed from mullite series alumina is arranged the spacing between two layers 55a and 55b, and also between anode electrode 58 and reference electrode 59.

Here, a constant voltage (for example, 0.6V) of a direct current power source 61 is applied between cathode electrode 57 and anode electrode 58.

Then, a limiting current (pumping current) Ip flowing is detected based on a terminal voltage of a current detection resistor R.

Further, an electromotive force generated between cathode electrode 57 and reference electrode 59 is output as a sensor electromotive force Ec via a differential amplifier 62.

Note, an area where cathode electrode 57 faces anode electrode 58 substantially equals an area where cathode electrode 57 faces reference electrode 59.

Further, a resistance value of a pumping portion is set to be 50 to 100 Ω under an arbitrary temperature condition.

In the above constitution, when the air-fuel ratio of the engine is leaner than the stoichiometric air-fuel ratio, since a large amount of oxygen remains in the exhaust gas, in cathode electrode 57, electrons are given to the oxygen remaining in the exhaust gas to generate oxygen ions.

Then, the oxygen ions are transported toward anode electrode 58 via zirconia solid electrolyte layer 55 (55a), to be decomposed into oxygen and electrons in anode electrode 58.

Figure 7:
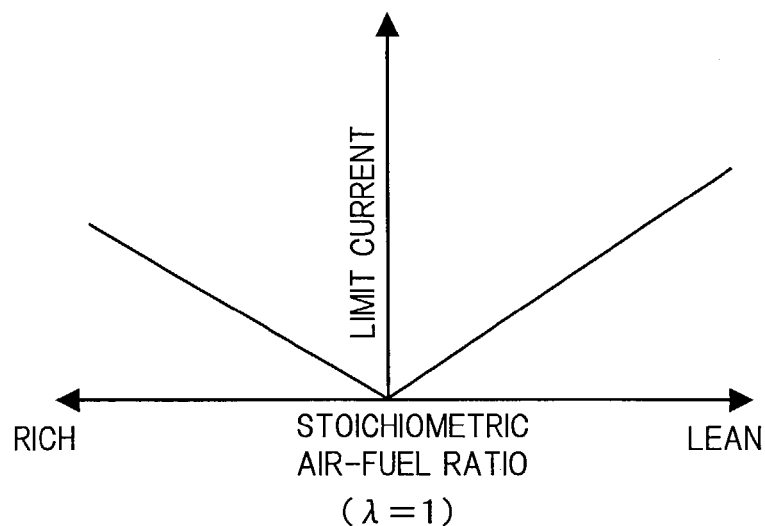
FIG. 7 is a graph showing a correlation between a limiting current and an air-fuel ratio in the sensor element shown in FIG. 5.

Thus, the limiting current (pumping current) Ip that is increased as the air-fuel ratio is leaner flows between cathode electrode 57 and anode electrode 58, as shown in FIG. 7.

On the other hand, when the air-fuel ratio of the engine is richer than the stoichiometric air-fuel ratio, although oxygen is little, but concentrations of hydrogen ($H_2$), carbon monoxide (CO) and hydrocarbon (HC) are high. Therefore, electrons are given to carbon dioxide and water in cathode electrode 57, to generate oxygen ions.

Then, the oxygen ions are transported toward anode electrode 58 via zirconia solid electrolyte layer 55 (55a), and in anode electrode 58, the oxygen ions transported from cathode electrode 57, and carbon monoxide and hydrogen in the exhaust gas react with each other, to be decomposed into carbon dioxide, water and electrons.

Thus, the limiting current (pumping current) Ip that is increased as the air-fuel ratio is richer flows between cathode electrode 57 and anode electrode 58, as shown in FIG. 7.

As described in the above, the limiting current (pumping current) Ip is increased as the air-fuel ratio becomes leaner, but is increased as the air-fuel ratio becomes richer.

Therefore, the air-fuel ratio cannot be detected based only the limiting current (pumping current) Ip, and accordingly, it is necessary to perform the rich/lean judgment of air-fuel ratio.

Note, the oxygen partial pressure of reference electrode 59 equals the oxygen partial pressure in the exhaust gas. However, in the lean air-fuel ratio state, as a result that the oxygen ions are transported toward anode electrode 58 from cathode electrode 59, the oxygen partial pressure of cathode electrode 57 becomes lower than the oxygen partial pressure in the exhaust gas.

Figure 8:
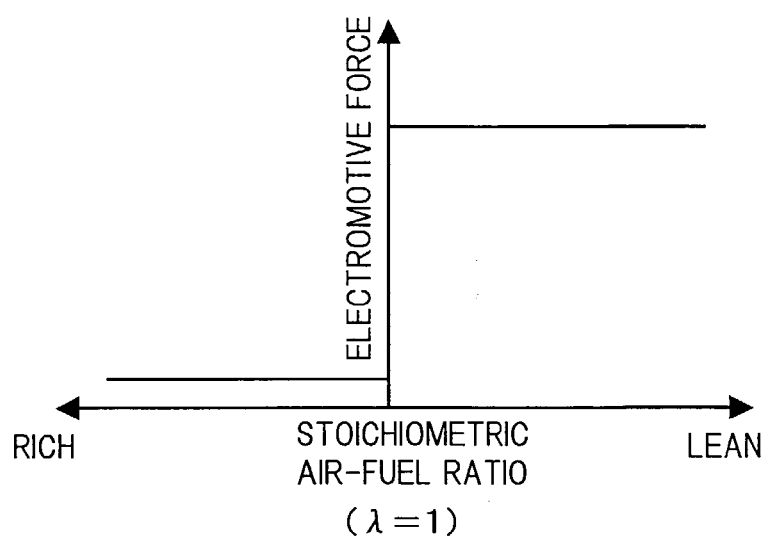
FIG. 8 is a graph showing a correlation between an electromotive force and the air-fuel ratio in the sensor element shown in FIG. 5.

Accordingly, in the lean air-fuel ratio state, there occurs a difference between the oxygen partial pressure of reference electrode 59 and the oxygen partial pressure of cathode electrode 57, to generate an electromotive force (refer to FIG. 8).

In the rich air-fuel ratio state, since the oxygen partial pressures of reference electrode 59 and cathode electrode 57 is substantially 0, and accordingly, there is no difference between the oxygen partial pressures of reference electrode 59 and cathode electrode 57, an electromotive force is not substantially generated (refer to FIG. 8).

Consequently, it is possible to judge that the air-fuel ratio is lean when the sensor electromotive force Ec is higher than a threshold, and that the air-fuel ratio is rich when the sensor electromotive force Ec is lower than the threshold.

Then, based on such rich/lean judgment result and the limiting current (pumping current) Ip at that time, the rich air-fuel ratio or the lean air-fuel ratio can be detected.

Note, since zirconia solid electrolyte layer 55 is divided into two layers 55a and 55b along the axial direction, it is possible to prevent electric current flowing into reference electrode 59 from anode electrode 58.

Thus, it is possible to accurately generate an electromotive force according to the difference between the oxygen partial pressure of reference electrode 59 and the oxygen partial pressure of cathode electrode 57, thereby enabling to judge the rich/lean of air-fuel ratio with high accuracy.

Further, since dense layer 60 is arranged on the portion where zirconia solid electrolyte layer 55 is divided into two, it is possible to prevent the gas diffusion via the divided portion, thereby enabling to avoid the degradation of detection accuracy due to the division of zirconia solid electrolyte layer 55.

In the above embodiment, the sensor element of rod shape has been used, however, a similar effect can be achieved with a similar constitution if a sensor element of plate shape is used.

The entire contents of Japanese Patent Application No. 2002-142749, filed May 17, 2002, and Japanese Patent Application No. 2002-143154, filed May 17, 2002, priorities of which are claimed, are incorporated herein by reference.

While only selected embodiments have been chosen to illustrate the present invention, it will be apparent to those skilled in the art from this disclosure that various change and modification can be made herein without departing from the scope of the invention as defined in the appended claims.

Furthermore, the foregoing descriptions of the embodiments according to the present invention are provided for illustration only, and not for the purpose of limiting the invention as defined by the appended claims and their equivalents.

What is claimed are:

1. An oxygen sensor comprising:
   a solid electrolyte layer having an oxygen ion conductivity;
   a pair of pumping electrodes formed to face each other with said solid electrolyte layer therebetween;
   a reference electrode formed to face one of said pair of pumping electrodes with said solid electrolyte layer therebetween;
   an oxygen supply power source that applies, between said reference electrode and said one pumping electrode, a voltage for supplying oxygen to said reference electrode;
   a dense layer covering said reference electrode, and
   one and the other outputs, the one being configured to output an electromotive force generated between the one pumping electrode and the reference electrode as a first detection signal first, and the other being configured to output a limiting current flowing between the pair of pumping electrodes as a second detection signal,
   wherein a gas diffusion layer is formed annularly on a periphery of a rod shaped base; and the solid electrolyte layer, the dense layer, the pair of pumping electrodes and the reference electrode are formed annularly on a periphery of the gas diffusion layer.

2. An oxygen sensor according to claim 1,
   wherein the dense layer is formed from mullite series alumina with an average grain size of 0.3 to 0.5 µm.

3. An oxygen sensor according to comprising:
   a solid electrolyte layer having an oxygen ion conductivity;
   a first and second pumping electrodes formed to face each other with said solid electrolyte layer therebetween;
   a reference electrode formed to face one of said pair of pumping electrodes with said solid electrolyte layer therebetween;
   an oxygen supply power source that applies, between said reference electrode and the first pumping electrode, an electric voltage for supplying oxygen to said reference electrode;
   a dense layer covering said reference electrode, and
   one and another outputs, the one being configured to output an electromotive force generated between the one pumping electrode and the reference electrode as a first detection Signal first, and the other being configured to output a limiting current flowing between the pair of pumping electrodes as a second detection signal;
   wherein a heater pattern, an insulating layer, a first gas diffusion layer and the solid electrolyte layer are laminated on the outside of a base, in this sequence,
   a second gas diffusion layer and the dense layer which are disposed to face each other are disposed to cover an outside of the solid electrolyte layer,
   the second pumping electrode is formed on the outside of the solid electrolyte layer covered by the second gas diffusion layer;
   the first pumping electrode is formed on an inside of the solid electrolyte layer facing the second pumping electrode; and
   the reference electrode is formed on the outside of the solid electrolyte layer covered by the dense layer.

4. An oxygen sensor according to claim 3,
   wherein the first and second gas diffusion layers are formed from alumina and zirconia based ceramic mixed powder with an average grain size of 0.4 to 0.8 µm.

5. An oxygen sensor comprising:
   a solid electrolyte layer having an oxygen ion conductivity;
   a pair of pumping electrodes formed to face each other with the solid electrolyte layer therebetween;
   a reference electrode formed to face one of said pair of pumping electrodes with the solid electrolyte layer therebetween;
   a dense layer dividing the solid electrolyte layer between the other pumping electrode and the reference electrode,
   a first output configured to output an electromotive force generated between the one pumping electrode to which the reference electrode faces and the reference electrode as a first detection signal; and
   a second output configured to output a limiting current flowing between the pair of pumping electrodes as a second detection signal.

6. An oxygen sensor according to claim 5,
   wherein an annular inner gas diffusion layer, the solid electrolyte layer and an annular outer gas diffusion layer are laminated on a periphery of a rod shaped base, in this sequence, a pumping electrode on a cathode side is annularly formed on the inside of the solid electrolyte layer, and also a pumping electrode on an anode side and the reference electrode are formed annularly on the outside of the solid electrolyte layer.

7. An oxygen sensor according to claim 5, wherein
   a heater pattern, an insulating layer, a first gas diffusion layer, the solid electrolyte layer, and a second gas diffusion layer are laminated on the outside of a base, in this sequence:
   the solid electrolyte layer consists of two solid electrolyte layers disposed in parallel with each other with predetermined spacing therebetween;
   a first pumping electrode is formed on the inside of the solid electrolyte layer so as to lie across said two solid electrolyte layers;

the second pumping electrode is disposed on the outside of one of the two solid electrolyte layers, and the reference electrode is disposed on the outside of the other of the two solid electrolyte layers; and the dense layer is disposed between the two solid electrolyte layers, and also between the second pumping electrode and the reference electrode.

8. An oxygen sensor according to claim 5, wherein a spacing between the divided two solid electrolyte layers is 0.3 to 0.5 mm.

9. An oxygen sensor according to claim 5, wherein an area where the one pumping electrode faces the other pumping electrode with the solid electrolyte layer therebetween and an area where the one pumping electrode faces the reference electrode with the solid electrolyte layer therebetween are set to equal each other.

10. An oxygen sensor according to claim 5, wherein a resistance value between the pumping electrodes is set to be 50 to 100 Ω.

11. An oxygen sensor according to claim 5, wherein the dense layer is formed from mullite series alumina.

* * * * *